United States Patent
Lee

(10) Patent No.: US 6,436,074 B1
(45) Date of Patent: Aug. 20, 2002

(54) GARMENT FOR SECURING AND EXPOSING A PERITONEAL DIALYSIS CATHETER AND CATHETER EXIT SITE

(76) Inventor: Jarrel Eugene Lee, 4001 Whirlwind Dr., Bakersfield, CA (US) 93313

( * ) Notice: Subject to any disclaimer, the term of this patent is extended or adjusted under 35 U.S.C. 154(b) by 0 days.

(21) Appl. No.: 09/724,372

(22) Filed: Nov. 28, 2000

Related U.S. Application Data

(63) Continuation of application No. 09/588,011, filed on Jun. 6, 2000, now abandoned.
(60) Provisional application No. 60/138,012, filed on Jun. 8, 1999.

(51) Int. Cl.[7] ............................................... A61M 5/32
(52) U.S. Cl. ........................ 604/174; 604/179; 128/876
(58) Field of Search ................................ 604/174, 175, 604/179; 128/877, DIG. 26

(56) References Cited

U.S. PATENT DOCUMENTS

| | | | | |
|---|---|---|---|---|
| 4,416,664 A | * | 11/1983 | Womack | 604/179 |
| 4,569,348 A | * | 2/1986 | Hasslinger | 604/179 |
| 4,571,245 A | * | 2/1986 | Hubbard | 604/179 |
| 4,738,661 A | * | 4/1988 | Marut | 604/179 |

* cited by examiner

*Primary Examiner*—Michael A. Brown

(57) ABSTRACT

A torso belt is disclosed which enables replaceable sterilized gauze to be held in position at a peritoneal catheter stoma without the use of tape. By attaching a block of foam rubber to the inside of a torso belt, the gauze can be kept in place at the stoma even though a catheter is penetrating this same stoma, as long as the external end of the catheter is immobilized. This immobilization can be accomplished by placing the external end of the catheter into a securable pouch attached to the inside of the same belt.

1 Claim, 6 Drawing Sheets

Side of Flexbelt Facing the Torso

Side of Flexbelt Facing Away from the Torso

GARMENT FOR SECURING AND EXPOSING A PERITONEAL DIALYSIS CATHETER AND CATHETER EXIT SITE

CROSS-REFERENCE TO RELATED APPLICATIONS

This application is a continuation of Ser. No. 09/588,011 filed Jun. 6, 2000, now abandoned, which claims the benefit of No. 60/138,012 filed Jun. 8, 1999.

U.S. Patent Documents cited in this Specification:

| | | |
|---|---|---|
| 5,019,050 | 5/1991 | Lynn et al. |
| 4,955,867 | 9/1990 | Endo |
| 5,244,464 | 9/1993 | Madden et al. |
| 5,205,832 | 4/1993 | Tuman |
| 4,738,661 | 9/1986 | Marut |
| 4,569348 | 2/1986 | Hasslinger |
| 4,571,245 | 2/1986 | Hubbard |
| 4,416,664 | 11/1983 | Womack |

STATEMENT REGARDING FEDERALLY SPONSORED RESEARCH OR DEVELOPMENT

No Federally sponsored research or development is or was connected with this invention.

BACKGROUND OF THE INVENTION

1. Field of the Invention

This invention is a device designed for, but not limited to, chronic kidney failure patients able to utilize continuous peritoneal dialysis (CAPD) or continuous cyclic peritoneal dialysis (CCPD). The invention allows a patient to comfortably secure or replace, without the use of tape, sterilized gauze at the point where the catheter exits the abdomen.

2. Description of Prior Art

For chronic kidney failure patients, peritoneal dialysis may need to be carried out at a frequency ranging from several times a week to several times a day. After a peritoneal catheter has been permanently inserted into the abdomen, many of these patients are able to carry out the dialysis themselves at home.

During the peritoneal dialysis process, the catheter is first used for transferring dialysate or other solution into the patient's peritoneum. During this phase of the process, the portion of the catheter outside the abdomen is connected to either a bag of solution or a cyclic solution transfer machine. The catheter is then disconnected from the solution source. After the solution has absorbed toxins in the peritoneum, the portion of the catheter outside of the body is connected to a drain transfer line to transfer toxin-laden fluids from the peritoneum. This whole process typically lasts from a matter of hours to overnight.

After draining, the catheter is once again disconnected. Because small amounts of bodily fluids often seep from a stoma through which the catheter passes, the patient's next task is to clean the portion of the catheter outside of the body, as well as this stoma and the skin surface proximate to it (the "exit site"), and to place there a clean swatch of sterilized gauze. The gauze not only provides seepage absorption, but also reduces odors and helps provides a sanitary environment around the stoma. This gauze is normally kept in place over the exit site by being taped directly to the skin with surgical tape. Next the portion of the disconnected catheter line outside of the patient (the "catheter protrusion") is taped to the body so that it doesn't dangle irritatingly or get snagged on something and cause internal bleeding. Once this has been done, the patient is free to go about his or her daily activities until the next time dialysis is called for.

The problems associated with taping to the skin either the sterilized gauze or the catheter protrusion are as follows:
1. Taping can be irritating to some skin, especially when performed repeatedly in the same area.
2. Taping can be difficult. Tape can run out.
3. Taping can be time consuming for the patient performing dialysis.
4. Health care workers must take time to un-wrap and re-tape gauze over the exit site each time the site is inspected.
5. Taping gauze over an exit site will not, by itself, keep the catheter from moving relative to the stoma, with such movement causing possible injury.

At the exit site is a variable, three-dimensional topology created by the stoma/skin surface and the relatively thick and stiff type of catheter used for dialysis. Physicians require replaceable sterilized gauze adjacent to the exit site, and there is no obvious way, based upon prior art, to secure replaceable gauze at such a difficult exit site, other than through the use of tape. The current art calls for first shaping sterilized gauze around the exit site topology, and then taping the edges of the gauze directly to the skin while the catheter is as immobile as possible relative to the stoma.

Prerequisite to any new method of keeping the gauze securely in place at the exit site is still being able to keep the end of the catheter protrusion immobile. The end of the catheter protrusion must not dangle or snag. The common method of keeping the end of the catheter protrusion immobile calls for taping it directly to the torso. However, since the ultimate objective is to eliminate the use of tape, it is important to note several inventions have been documented which apply to this prerequisite immobilization of the end of the catheter protrusion:

In September 1990, Endo patented a "Perirtoneal Dialysis Catheter Belt" that consisted of a fabric or paper belt or band, which fastened around the abdomen, near the exit site. The belt had a pouch, which could be used to house and secure the very end of the catheter protrusion. However, the invention did not address the problem of taping gauze over the exit site, as addressed by this specification. To use Endo's invention, gauze must still be taped over the exit site.

In May 1991, Lynn et al. patented A "Securing Device and Method," consisting of a strap with hook and loop fasteners at each end, as well as a method for wrapping it around a limb. Using this method, however, is best suited to limbs, where the line runs along the length of the limb. Using this method, such a strap could conceivably be wrapped around the torso a sufficient number of times to secure the catheter protrusion positioned vertically up the torso, then wrapped a final time around and fastened again. The number and position of the windings around the torso would make this uncomfortable and would not hold the catheter securely through a wide range of motion.

In April, 1993, Tuman patented an "Endo-tracheal Tube support Device," also for securing lines running up the torso of the patient, rather than across the torso, as is needed. Similarly the 'Band for Securing and Aligning Medical Tubing" patented by Madden et al. in September 1993 and the "Catheter Tube Holder Strap" patented by Hasslinger in February 1986 and a "Catheter Securing Device" patented by Womack in November 1983 also secure lines running up the torso rather than across the torso. Although the Hubbard invention includes a gauze element, the gauze is (1) neither replaceable nor sterilized as required for sanitary purposes at an exit site, and (2) not intentioned to cover a peritoneal catheter exit site, where any application of Hubbard's invention would encounter the aforementioned topological problems.

A "Gastrostomy Belt" patented by Marut in April 1988 correctly addresses the need to secure the end of the catheter protrusion across the torso in a belt pouch, rather than along the torso's length. It provides to have the pouch made form an absorbent material. However, Marut does not put forth the idea of securing without tape replaceable sterilized gauze at the exit site, nor does the invention contribute to the this notion.

Although the inventions of Endo et al. and Marut could be used to provide the prerequisite immobilization of the end of the catheter protrusion, neither of these approaches addresses the elimination of taping the catheter and sterilized gauze at the exit site as presented here.

No previous invention either recognizes or serendipitously solves any of the aforementioned problems associated with taping gauze over a catheter exit site.

SUMMARY OF THE INVENTION

The invention is a device consisting of (1) an elastic strap which can be fastened into a torso belt using Velcro® fasteners, this torso belt having a block of foam rubber, or similar material attached beneath one end of it, this block being capable of contouring to the topology of the exit site as it exists after replaceable sterilized gauze has been placed over the exit site, and (2) a pouch on the torso belt, starting at the exit site covering and running the along the belt, of sufficient length to contain within the pouch all of a patient's catheter protrusion, the pouch opening once at its top along the length of the pouch and again through a slit at the exit site covering. It is the block of foam rubber, thus strapped over the exit site, which keeps the replaceable gauze in place without the use of tape, so long as the end the catheter protrusion is kept immobile by placing it in its pouch.

To don the device, first the end of the patient's catheter protrusion is threaded through the slit and into the pouch. Next, the patient holds sterilized gauze in place over the exit site. With the foam rubber being positioned directly over the exit site topology, the belt is fastened loosely around the torso. This loose fastening immobilizes the end of the catheter protrusion relative to both the removable gauze and the stoma. The patient releases the gauze and the belt is tightened to secure. At once the catheter line is entirely protected and disabled from dangling or snagging and the gauze is held in place over the exit site by the foam rubber. At no time is any tape employed, thereby eliminated associated problems.

At any time, the catheter's connector is available for use by simply opening the pouch at its top, and accessing it. The exit site is available for examination by simply loosening the belt slightly and sliding the belt up or down the torso.

The device is very particularly combined from three constituent parts: (1) a torso belt, (2) a pouch along that belt, and (3) a block of foam rubber, or similar material shapeable to the exit site topology. Whenever the device is donned as heretofore described, the functionality of each of the three individual parts combine to form a new and unique fourth functionality characteristic of the device as a whole. Namely, this new and unique functionality secures, without the use of surgical tape, replaceable sterilized gauze over a peritoneal catheter stoma, and does so while allowing the patient's catheter extension to be either connected, or disconnected and secured to the torso.

The new and unique functionality provides the user a new and unique benefit by solving the gauze taping problems which prior art has not recognized or solved. In addition, the invention allows the catheter to be connected and disconnected without adding or removing any tape to the torso, thereby eliminating not only gauze taping, but all taping associated with peritoneal dialysis.

Neither this noted new and unique functionality nor its benefit is a sum of any collection of functions and benefits of the device's three constituent parts, as none of the functions and benefits of the device's parts suggest or anticipate either the invention's new and unique functionality or its benefit. On the contrary, the invention is not obvious, requiring the discovery of the taping problem, a characterization of the exit site topography, and a device especially designed for the new and unique purpose of solving the taping problem.

DETAILED DESCRIPTION OF THE ILLUSTRATED EMBODIMENT

Figure 1:
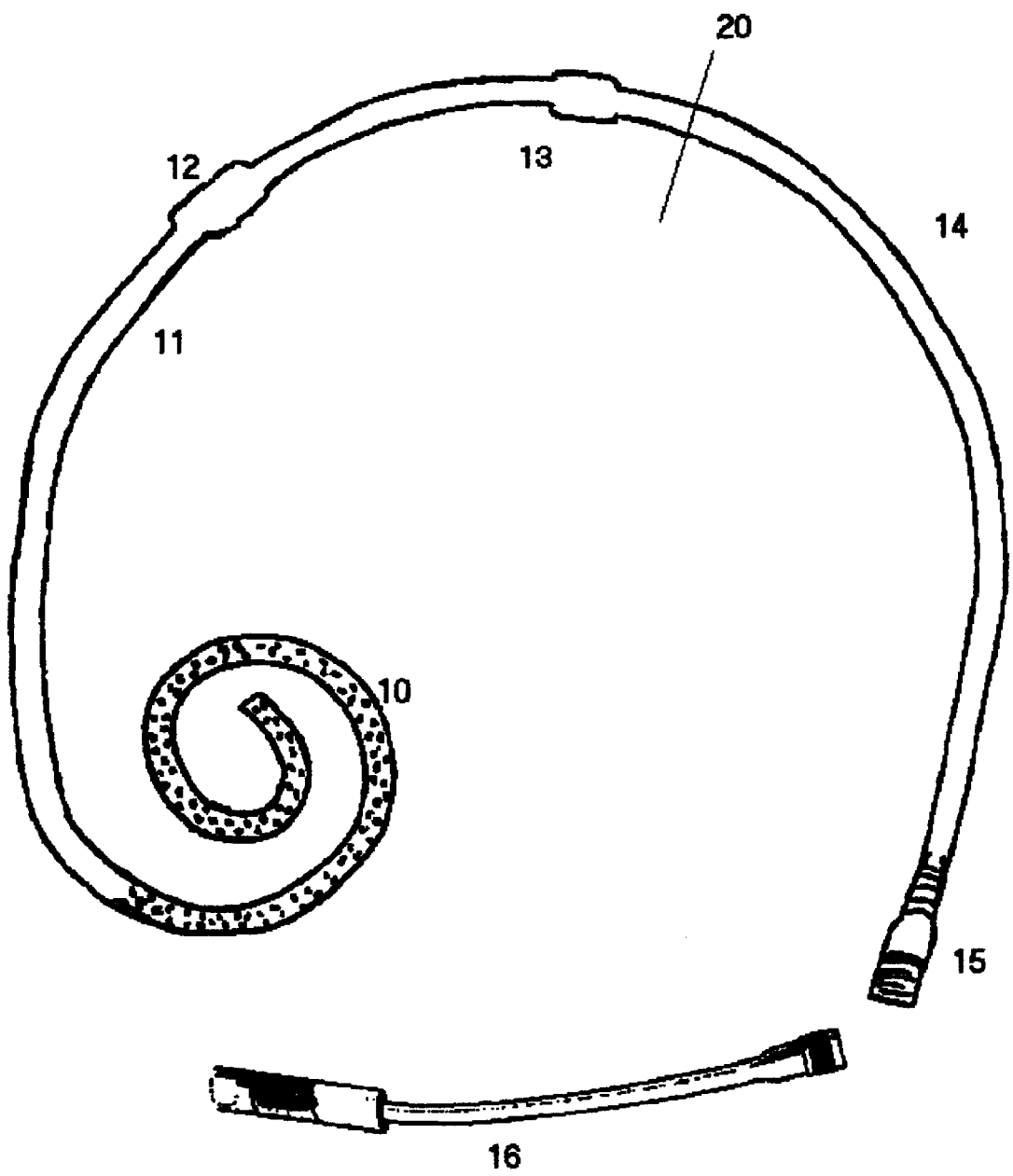
FIG. 1 is a diagram of a complete peritoneal catheter and transfer line.
Figure 2:
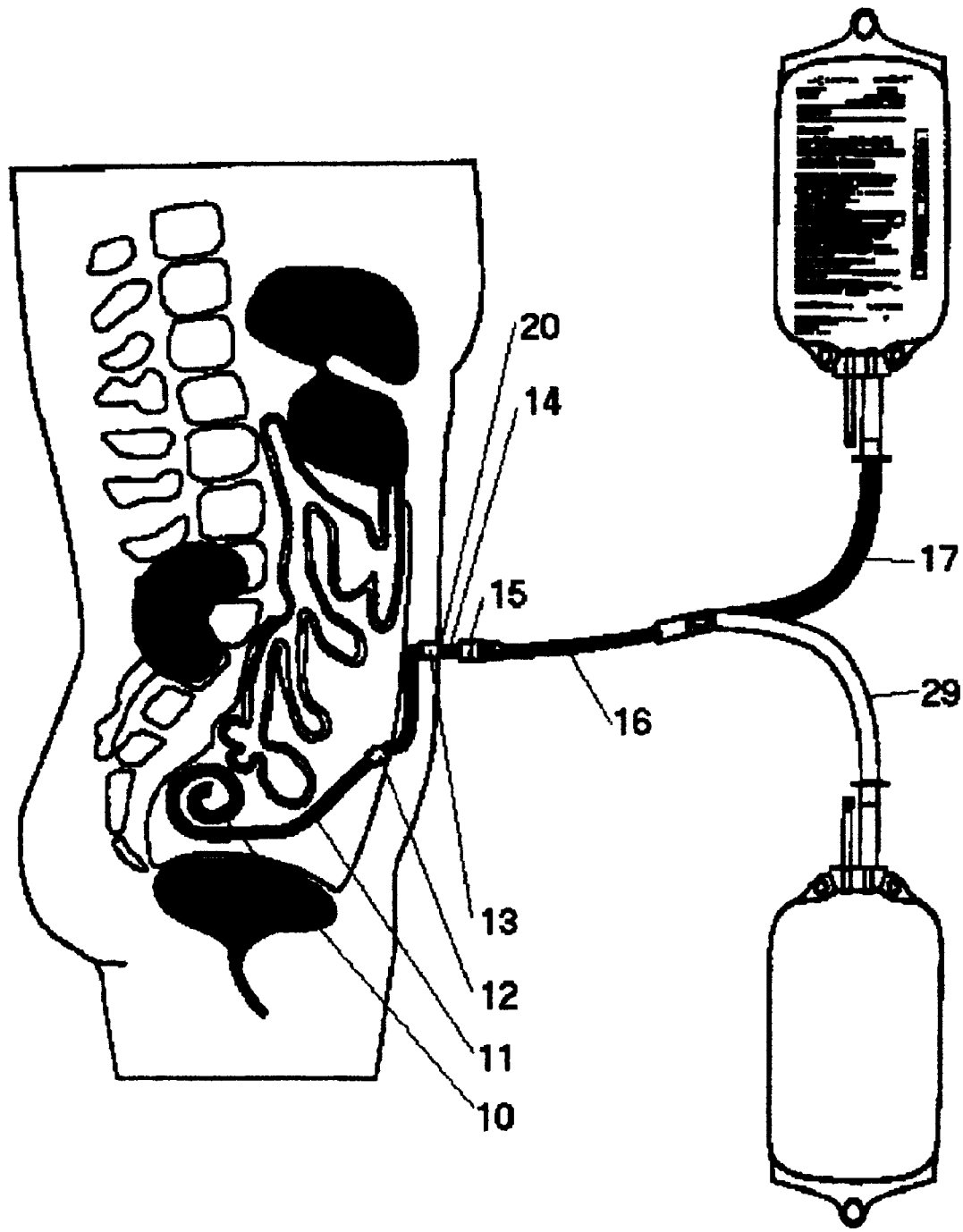
FIG. 2 is a schematic of a peritoneal catheter as it resides in the body, protrudes from the abdomen, and is attached to either a solution bag or drain.

As shown in FIG. 1 and FIG. 2, the peritoneal catheter consists of several parts 10, 11, 12, and 13, which are permanently inside the body, and a protrusion outside the body consisting of catheter tubing 14 and a titanium connector 15. During dialysis the connector 15 is connected to a transfer line 16, which is in turn connected to either a solution line 17 or a drain line 29, often via a cyclic machine (not pictured).

Figure 3:
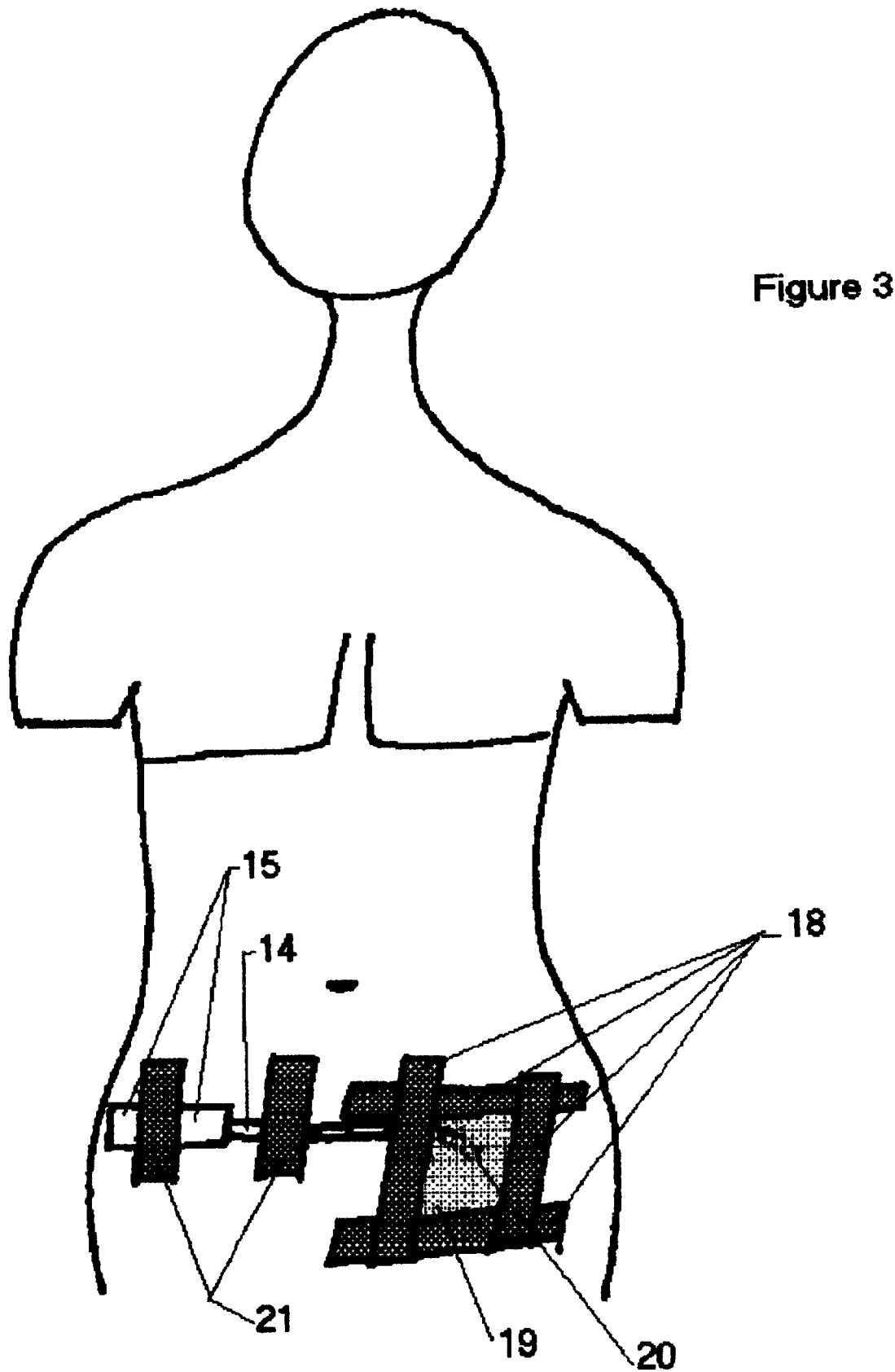
FIG. 3 is a diagram of the usual method of taping the gauze and catheter protrusion to the body after dialysis has been completed.

As depicted in FIG. 3, when the dialysis has been completed, the patient normally uses surgical tape 18 to tape replaceable sterilized gauze 19 over the exit site 20. The catheter protrusion's tubing 14 and connector 15 are also taped to the skin with surgical tape 21.

Figure 4:
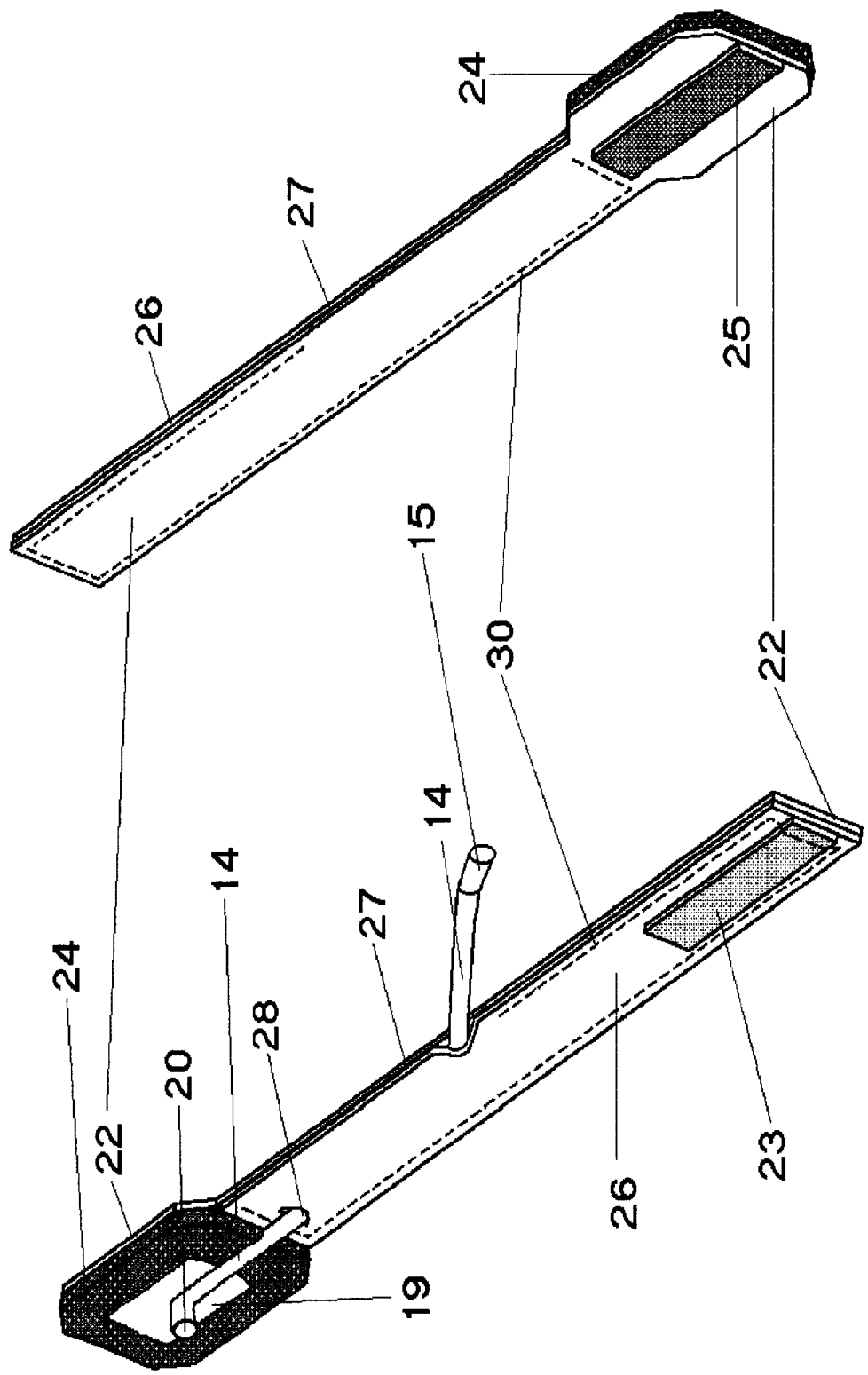
FIG. 4 us a diagram of the skin-side view of the invention showing where the catheter protrusion enters the pouch at the slit and may exit the pouch on top for inspection or connection. Separately depicted is the outside view of the invention without a catheter protrusion.

As depicted in FIG. 4, the invention consists of a strap 22 made from a durable slip-resistant material, and with hook-and-loop fasteners 23 and 25 at each end. Beneath the strap is attached a gauze covering 24 consisting of block of foam rubber sufficient in size to keep the catheter and the replaceable gauze immobile during daily use. A pouch 26 runs the length of the strap starting at the foam rubber, and of sufficient length to hold the patient's catheter protrusion tubing 14 and connector 15. The pouch 26 has an opening 27 all along its top edge. In addition the pouch has a slit 28 located near the exit site 20. When worn, the patient's catheter protrusion tubing 14 exits the body at the exit site 20 and is threaded through the slit 27 and into the pouch 26. The connector 15 can be pulled out of the pouch's top opening 27 at any time for easy access.

Figure 5:
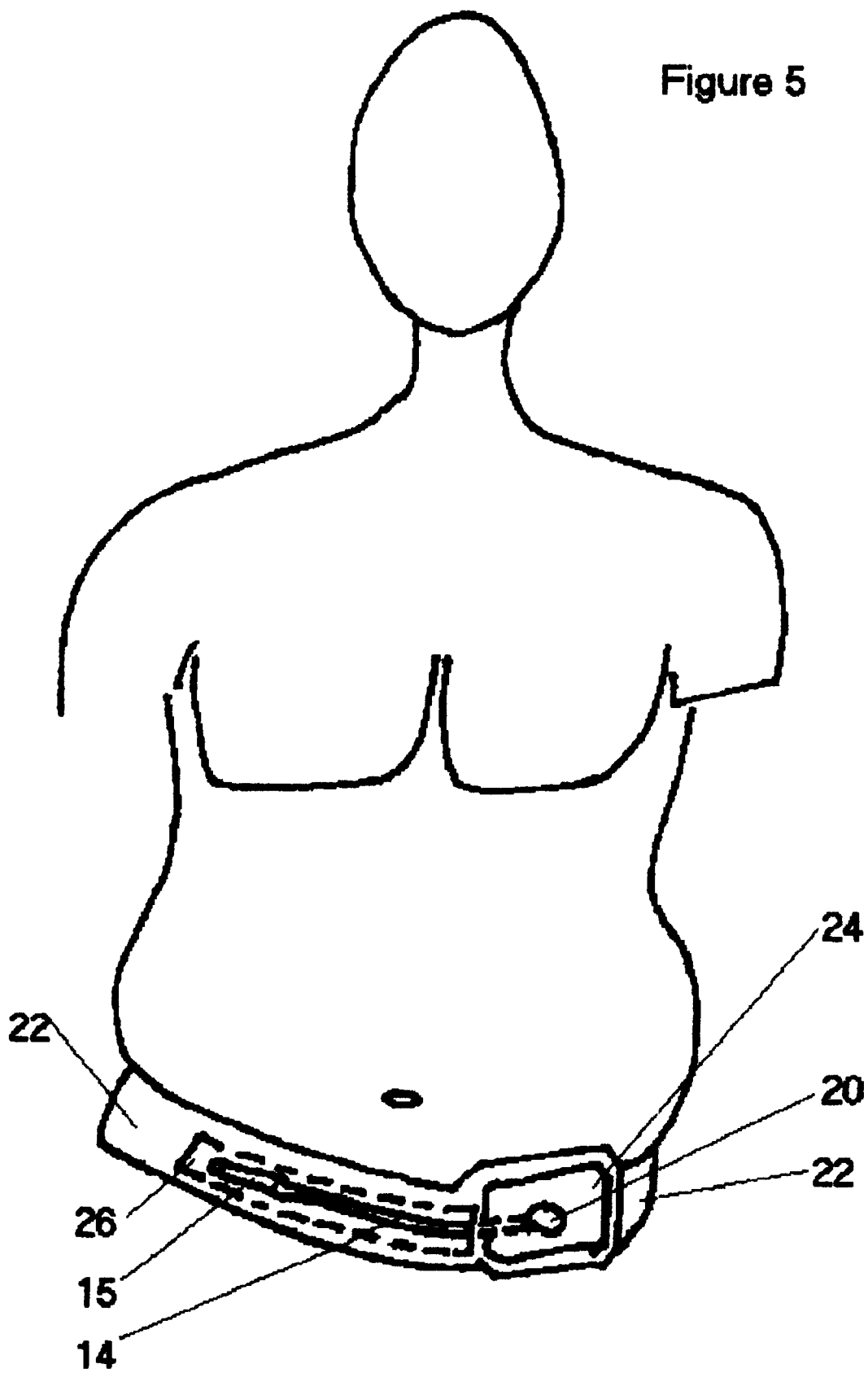
FIG. 5 is a drawing of the invention being worn, the foam block over the exit site and gauze, and with the catheter protrusion in the pouch.
Figure 6:
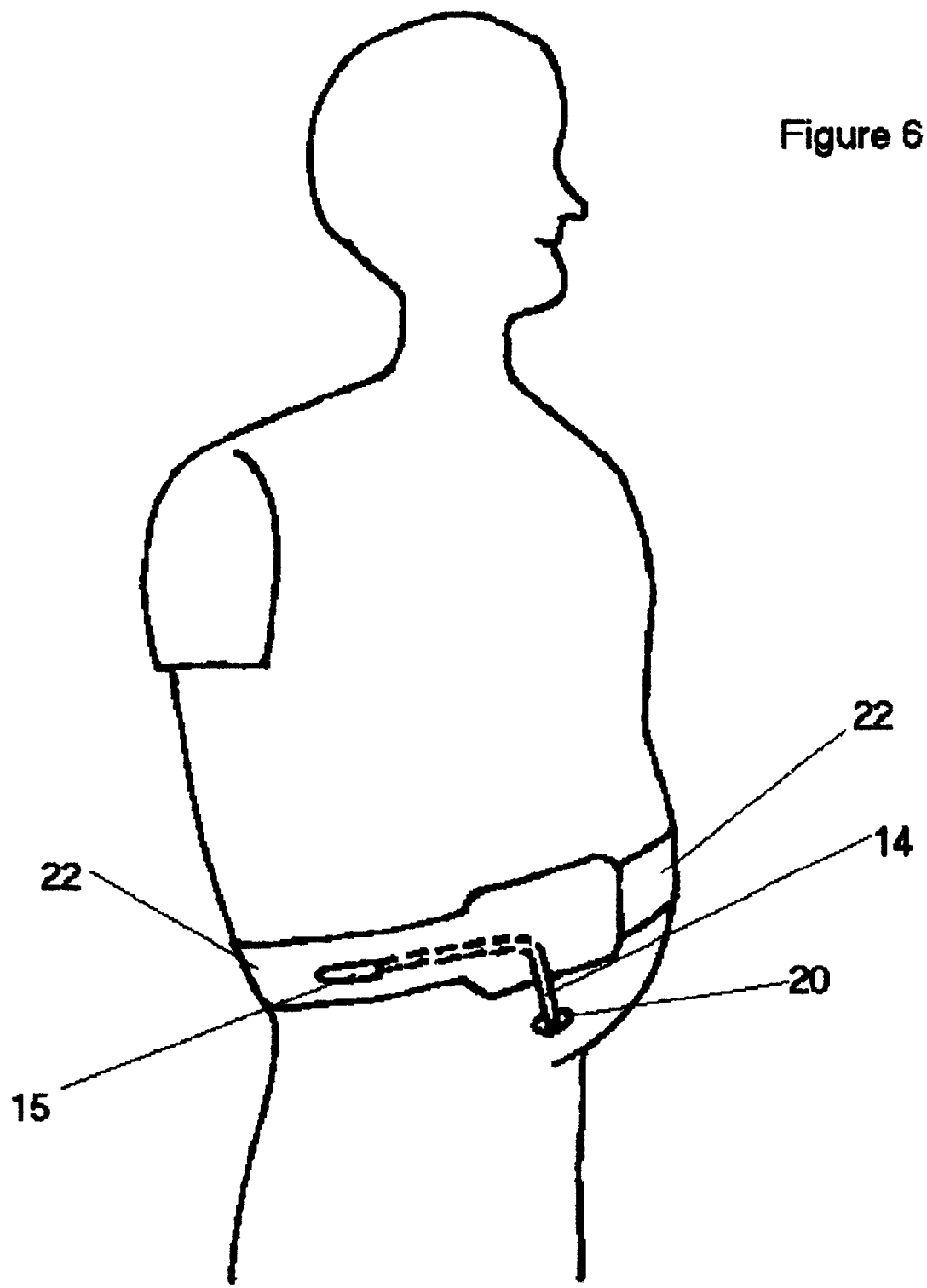
FIG. 6 is a drawing of the invention having been slipped up the torso to allow inspection of the exit site.

FIG. 5 shows the same invention in relation to the exit site and torso.

I claim:

1. A device to secure, without the use of surgical tape, replaceable sterilized gauze over a peritoneal catheter at the stoma, consisting of (1) a slip resistant torso belt, (2) a pouch permanently attached along the inside of this same belt, into which the end of the disconnected peritoneal catheter can be placed, and (3) a block of foam rubber permanently attached inside the belt, which, when placed over the stoma, the catheter at the stoma, and the replaceable gauze at the stoma, conforms to the underlying shape in order to secure the gauze in place over the stoma whenever both the belt is fastened firmly around the torso, and the end of the catheter protrusion is immobilized in the pouch.

* * * * *